United States Patent [19]
Hixson, Sr.

[11] Patent Number: 5,136,623
[45] Date of Patent: * Aug. 4, 1992

[54] MAMMOGRAPHIC SPOT COMPRESSION AND MAGNIFICATION PLATFORM AND MOUNTING THEREFOR

[75] Inventor: Gordon L. Hixson, Sr., Chattanooga, Tenn.

[73] Assignee: American Mammographics, Inc., Chattanooga, Tenn.

[*] Notice: The portion of the term of this patent subsequent to Aug. 13, 2008 has been disclaimed.

[21] Appl. No.: 736,068

[22] Filed: Jul. 25, 1991

Related U.S. Application Data

[63] Continuation-in-part of Ser. No. 591,563, Oct. 2, 1990, Pat. No. 5,040,198.

[51] Int. Cl.$^5$ ............................................. A61B 6/04
[52] U.S. Cl. ..................................... 378/37; 378/208; 378/209
[58] Field of Search .......................... 378/37, 208, 209

[56] References Cited

U.S. PATENT DOCUMENTS 5,040,198  8/1991  Hixson, Sr. ............................ 378/37

Primary Examiner—Janice A. Howell
Assistant Examiner—Don Wong
Attorney, Agent, or Firm—Alan Ruderman

[57] ABSTRACT

A spot compression and magnification device for use with mammographic units to aid in the spot compression of a female patient's breast to obtain a high degree of focal breast compression and a high quality x-ray image of a suspicious mass within the breast. The device has a base including an open bottom and an upstanding pedestal opening into the base, the pedestal having a flat top surface so that an air gap is provided between the top surface of the pedestal and the surface of the imaging platform or cassettes cover of a conventional mammographic unit. The pedestal has a substantially truncated conical form while the base has a substantially truncated pyramid configuration. Clamping handles are resilientlty attached to portions of the base to permit the handles to be pulled away from the base and be urged into clamping engagement in conjunction with the bottom edge of the base against the cassette cover.

16 Claims, 2 Drawing Sheets

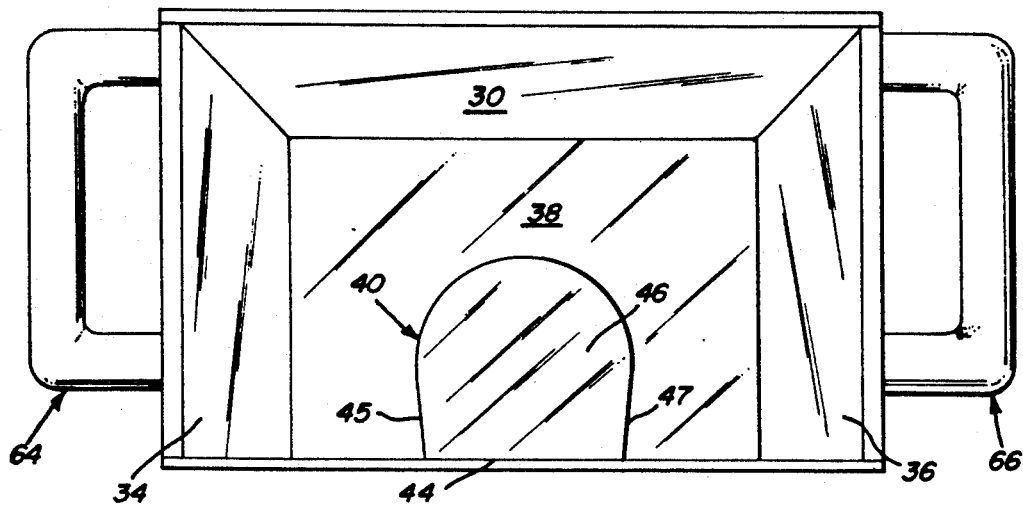
FIG. 3
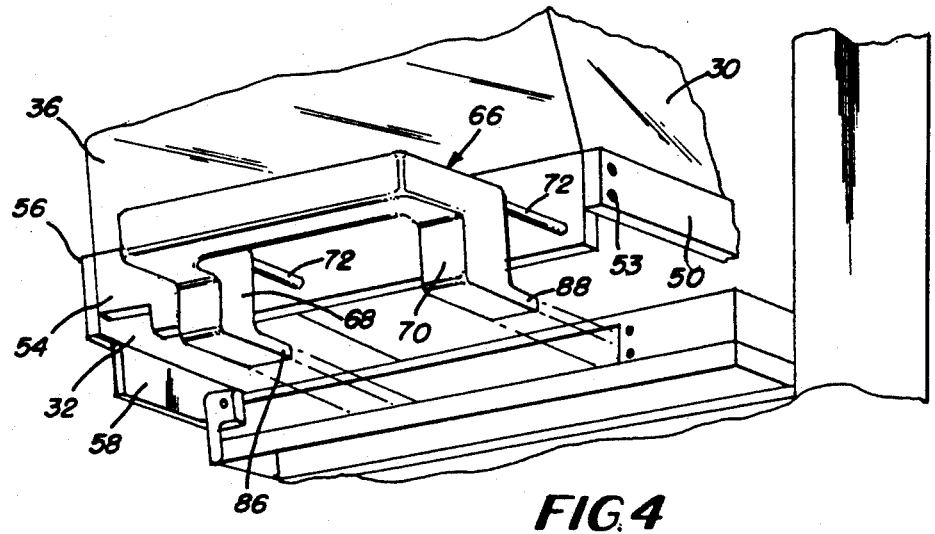
FIG. 4
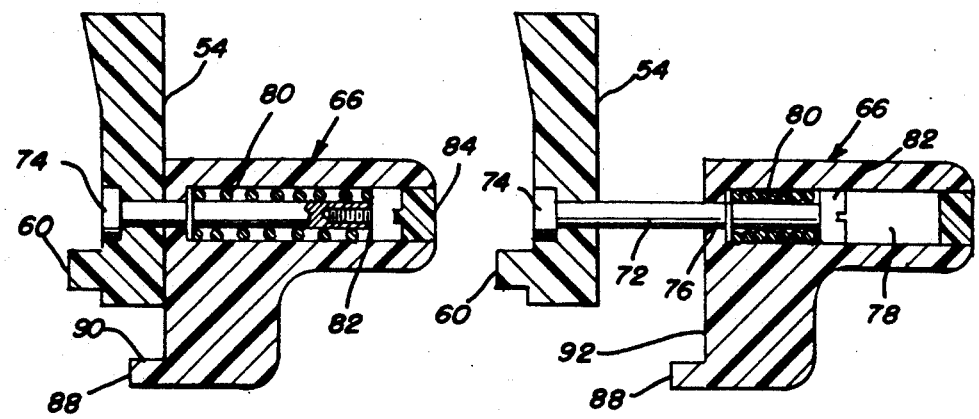
FIG. 5
FIG. 6

MAMMOGRAPHIC SPOT COMPRESSION AND MAGNIFICATION PLATFORM AND MOUNTING THEREFOR

REFERENCE TO RELATED APPLICATIONS

This application is a continuation-in-part of copending U.S. application Ser. No. 07/591,563 filed Oct. 2, 1990, now U.S. Pat. No. 5,040,198.

BACKGROUND OF THE INVENTION

This invention relates to mammography and more particularly to a spot compression and magnification platform for aiding in compressing a small area of the breast of a woman undergoing a mammographic examination to displace glandular structure and enhance the quality of the image made by the mammography x-ray apparatus, and to a mounting base for adjustable attachment of the spot compression and magnification platform to the supporting platform of the mammographic unit.

The x-ray detection of the breast, known as mammography, can provide a sensitive and satisfactory means for examining women when screening for breast cancer, an abnormality which affects a significant percentage of the female population. The predictability of the results of the procedure, which is predicated upon an interpretation of the x-ray image produced, and thus the quality of the image, may in certain cases be indefinite and thus inconclusive. For example, many of the abnormal or suspicious soft tissue densities demonstrated are neither clearly benign nor malignant. Cancers, benign tumors, cysts, and asymmetrical areas of glandular tissue can all have similar appearances. Consequently, breast biopsies subsequent to mammographic examination using conventional compression of the breast disclose a relatively low positive yield for cancer, ranging from ten percent to thirty percent. Thus, it has been demonstrated that equivocal mammographic abnormalities require supplemental diagnostic procedures to avoid unnecessary breast biopsy.

One of the most useful additional procedures is a spot compression view which is performed with a small compression paddle to compress only a small area of the breast to increase the accuracy of the image and confidence of the interpretation, the small compression paddle being substituted for a larger conventional paddle. A spot compression view spreads apart glandular structures which can simulate a mass or hide the margins of a true mass. Such views can better define a mass seen on a routine view, and also distinguish abnormalities from those caused by superimposition of normal breast tissue. In the majority of cases a spot compression view shows the suspicious soft tissue density to be benign thereby eliminating unnecessary additional mammographic examination necessitating an additional dose of x-rays, and/or breast biopsy.

Conventional mammographic views utilize a large flat compression paddle which is pushed against the upper portion of the breast to compress the breast between the paddle and the imaging platform of the mammography apparatus. A smaller compression paddle is conventionally used to compress a small area over a potential abnormality in the breast when spot compression views are performed. All of the known compression paddles in the prior art are mechanically attached for use to the adjustable vertical column of the mammographic unit above the breast. When a suspicious area is located on an x-ray, the standard paddle is removed and replaced by the smaller spot compression paddle, which as aforesaid provides a localized compression and a higher quality view by moving normal glandular structure or tissue from dispositions which may be superimposed relative to the area of the breast which requires closer examination.

Many of the older mammographic units in operation do not have the capability of readily accepting spot compression paddles which, it is believed, are available only for the newer mammographic units. Because of the enormous capital expense required for acquiring such units, many hospitals and other diagnostic facilities having the older mammographic units have not made, and may be unable to make, such expenditures as are necessary. Additionally, even with those newer units that have spot compression paddles, because of the normal shape of a breast, i.e., the upper portion of the breast has a greater slope than the lower portion which is substantially horizontal, compression of the breast at the upper portion against the imaging platform may not provide as much clarity to the image as would appear to be the case were the breast to undergo additional spot compression from the lower portion. At least one manufacturer provides a rigid stool-like member for increasing the magnification of the image, but not for spot compression of the breast, the member being attachable to the image platform and having a large top portion on which the breast rests while the image is being made.

In copending application Ser. No. 07/591,563 filed Oct. 2, 1990, to issue on Aug. 13, 1991, as U.S. Pat. No. 5,040,198, I have disclosed a number of freestanding spot compression and magnification devices positionable on the imaging platform of conventional mammographic units to obtain high degrees of focal breast compression and high quality images of a mass. These devices have magnification platforms incorporating a spot compression pedestal which improves contrast and spatial resolution, and can disperse surperimposed normal glandular tissue which at times interfere with evaluation of an abnormal area of the breast. Devices constructed in accordance with the invention include an open bottom base having an upper platform including an opening about which an upstanding pedestal is disposed, the pedestal being open at the bottom and having a flat top surface upon which the breast of a patient may be disposed and compressed by a conventional mammographic paddle. An air gap is provided between the upper surface of the pedestal and the imaging platform of the mammographic unit and provides improved radiographic contrast resolution and magnification to the image.

In the specific form of the aforesaid invention an upstanding wall of the base had an opening to increase the flexibility of the device to ensure that there was substantial depression of the portion of the pedestal facing the patient. Although such an opening was believed necessary for proper depression of the pedestal particularly with prototype models, with improved manufacturing and assembly procedures it has been found that the opening can be eliminated without substantial reduction in results. Furthermore, the devices, as aforesaid were free standing, being positionable upon the imaging platform of conventional mammographic units without mechanical attachment thereto. Although such a free standing relationship is satisfactory for the low magnification devices, high magnification spot compression devices require the magnification platform to be attached to the imaging platform of the mammography unit, i.e., the normal breast supporting platform must first be disassembled by completely removing a cassette holder containing a moving grid called a "Bucky" tunnel device. The grid, as known in the art, acts similar to a filter and is required when non-magnified imaging is performed. The magnifying platform is then attached directly to the imaging platform and the film or the cassette holder is inserted between the imaging platform and the magnifying platform. Thus, conversion from a non-magnified or lower magnified platform to a high magnified platform is awkward and time consuming.

SUMMARY OF THE INVENTION

It is a primary object of the present invention to provide a spot compression and magnification device interposed between the breast of a female patient and the imaging platform of a mammographic unit, the device having a base positionable on the imaging platform, an upper platform and an upstanding pedestal extending from the upper platform and on which the breast is positioned for compression between the device and a conventional paddle pressing on the upper surface of the breast.

It is another object of the present invention to provide a spot compression and magnification device interposed between the breast of a female patient and the imaging platform of a mammographic unit, the device having a base positionable on the cassette holder and an upstanding pedestal upon which the breast is positioned, the base of the device having adjustable means for permitting it to be connected to the normal breast supporting platform of the mammographic unit so that it is not necessary to remove the cassette holder containing the moving grid.

It is a further object of the present invention to provide a spot compression and magnification device interposed between the breast of a female patient and the imaging platform of a mammographic unit, the device having a base positionable on the cover of the x-ray film cassette, which is the normal breast supporting platform, and an upstanding pedestal on which the breast is positioned, the base of the device having clamping handles including locking tabs which adjustably engage into the opening or tunnel of the cassette holder to grasp the cover and secure the device in position.

Accordingly, the present invention provides a device as accessory for mammographic units for aiding in the spot compression of a female patient's breast to obtain a high degree of focal breast compression and magnification and thus to provide high quality x-ray images or views of a mass in the patient for greater diagnostic predictability. The device may be freestanding so as to be positionable upon the imaging platform of a conventional mammographic unit after removal of the cassette holder, but preferably is positionable directly upon the cassette holder within which a moving grid is carried, the latter being by means of adjustable clamping handles. The device includes a base having an open bottom and an upstanding pedestal opening into the base and having a peripheral wall extending from the upper surface or platform of the base. The adjustable clamping handles are movable relative to the base so that the device may be attached to a multiplicity of mammographic units without requiring removal of the cassette holder. The breast is positioned on the pedestal and is compressed between the device and a conventional mammographic paddle acting on the upper portion of the breast.

In the preferred form of the invention the adjustable handles are connected to the base by biasing means which permit the handles to be pulled away from the sides of the base yet urge the handles toward the base, the handles having tabs or tongues which enter into the tunnel of the film cassette when the base is supported on the cover thereof. The tongues having a ledge spaced beneath the base so as to abut the underside of the cassette cover when the base is disposed thereon.

BRIEF DESCRIPTION OF THE DRAWINGS

The particular features and advantages of the invention as well as other objects will become apparent from the following description taken in connection with the accompanying drawings in which:

FIG. 3 is a top plan view of the spot compression and magnification device;

FIG. 4 is a fragmentary perspective view of the bottom portion of the device at one end thereof illustrating the manner of mounting the device on the mammographic unit;

FIG. 5 is a cross sectional view through an adjustable clamping handle and a portion of the base of the device in the retracted or securing position; and FIG. 6 is a view similar to FIG. 5 but with the handle in the fully extended position permitting secure attachment of the base to a mammographic unit.

DESCRIPTION OF THE PREFERRED EMBODIMENT

Figure 1:
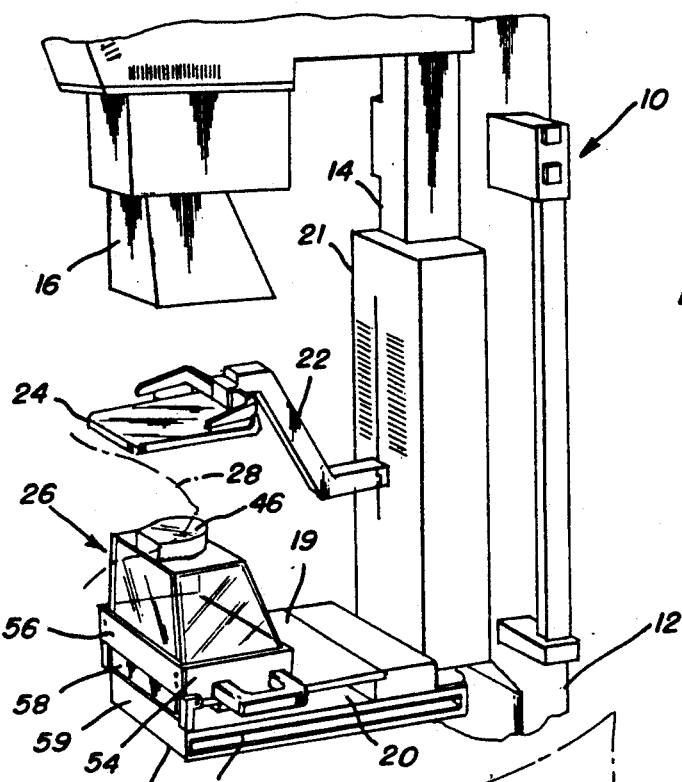
FIG. 1 is a fragmentary perspective view of a conventional mammographic unit with a spot compression and magnification device constructed in accordance with the principles of the present invention positioned on the cassette cover above the imaging platform thereof.

Referring now to the drawings, FIG. 1 illustrates a portion of a conventional relatively new type of mammographic unit 10, the unit comprising a frame 12 supporting a vertically adjustable column 14. The column 14 supports an overhanging head 16 which carries an x-ray source (not illustrated). Disposed below the head 16 is a vertically adjustable image platform 18, the platform generally having a cover member 19 disposed thereon and within which x-ray sensitive film is carried in, for example a film cassette (not illustrated) and a moving grid, the opening between the cover 19 and the surface of the image platform defining a "Bucky" tunnel 20, as well known in the art. Conventionally, the breast of a patient is placed on the cover member which forms a breast support platform, overlaying the the film. Disposed about the column 14 is a housing 21 to which the arm 22 of a standard compression paddle 24 is attached. The arm may be vertically adjusted to lower the paddle 24 onto the upper portion of the breast to compress it against the cover member 19, the adjustment in at least some units being effected by pneumatic means. A small paddle with its own arm may be substituted for the standard paddle when conventional spot compression x-ray images or views are to be made of a suspicious area within the breast, the smaller paddle acting to concentrate or localize the compression force on a smaller area of the breast for a higher quality view as heretofore described. As aforesaid in many of the older mammographic units in current use spot compression paddles are not provided, nor are they readily available, and the units do not appear to have the capability of receiving such spot compression paddles. Accordingly, in these older units a spot compression view cannot be obtained and the results of the procedure may be equivocal.

In accordance with one aspect of the present invention, a spot compression and magnification device 26 constructed in accordance with the preferred form of the invention, is disposed on the cover 19 of the platform 18 over the tunnel 20, and the compression paddle 24, either a standard or a spot compression paddle in those units having same, is lowered onto the breast 28 to compress the breast between the device 26 and the paddle 24 to obtain a high degree of focal breast compression. Thus, the device 26 of the present invention may be utilized with either the newer or older mammographic units, and in the latter case may provide spot compression capabilities, and magnification, not currently available for such units. As aforesaid, spot compression views are particularly significant for many patients.

Figure 2:
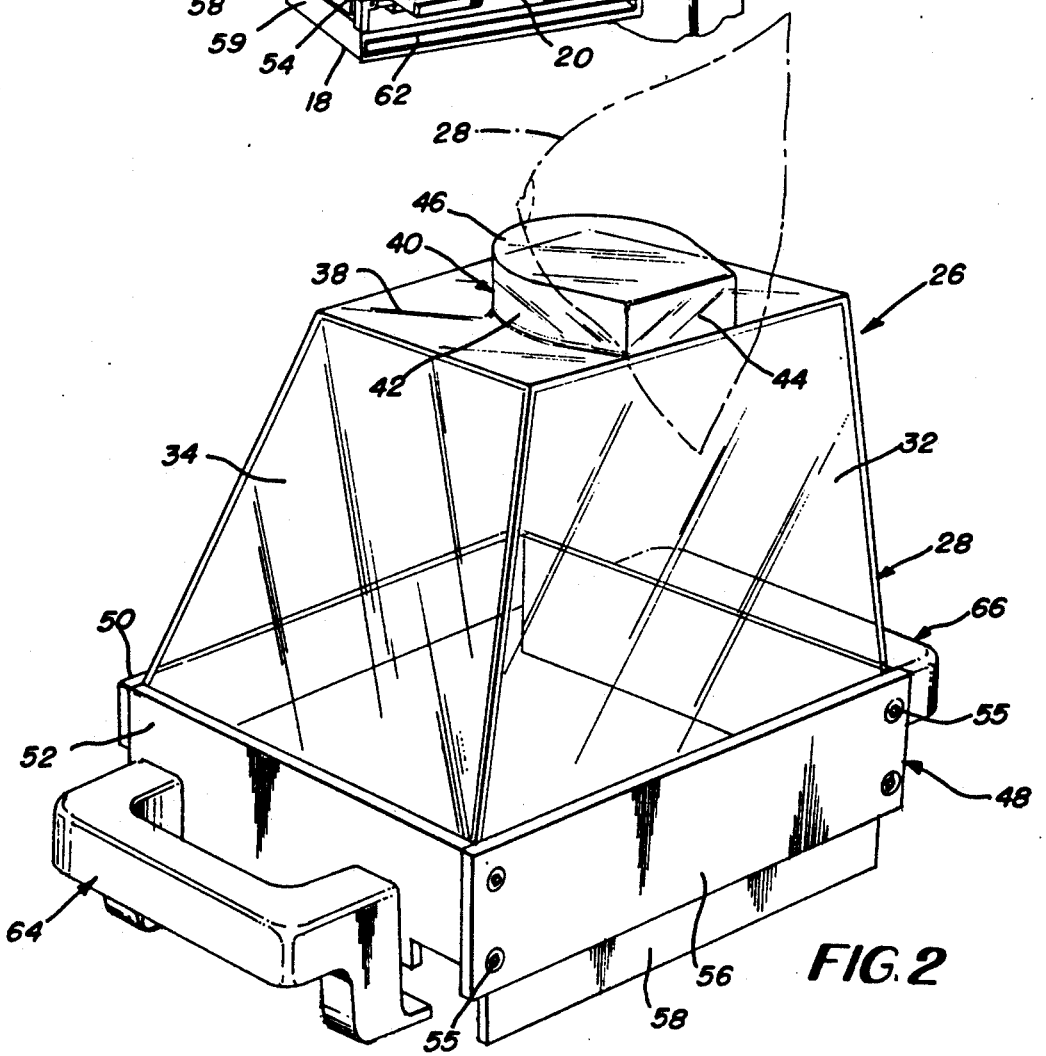
FIG. 2 is an enlarged perspective view illustrating the spot compression and magnification device illustrated in FIG. 1.

As illustrated in FIGS. 2 and 3, the device 26 comprises a base 28 having a substantially truncated pyramid configuration having a rectangular cross section including a front skirt 30 and a rear skirt 32 spaced apart by a pair of spaced apart end skirts 34, 36. The base, which is open at the bottom, includes an upper surface 38 having an aperture (not illustrated) formed therein, and a pedestal 40 is disposed on the upper surface overlying the aperture. The pedestal 40 is open at the bottom so as to open onto the interior of the base. Additionally, the pedestal 40 has a substantially truncated conical configuration with an upstanding peripheral wall 42. The peripheral wall 42 includes a flat rear portion 44 with the remaining portion being substantially circular, except adjacent to the rear portion 44 where there are a pair of flat surfaces 45, 47, a substantially flat upper surface 46 being disposed on the top of the wall 42 and conforming to the peripheral configuration thereof. The surfaces 45 and 47 could be circular, but for manufacturing ease they may be flat as illustrated. Thus, except for the flat rear portion 44, the pedestal is substantially conical.

The disposition of the pedestal is such that the bottom of the flat wall portion 44 may be very slightly offset from the rear skirt 32 of the base, or may be substantially aligned with the upper edge of the rear skirt 32, and although this disposition may vary slightly according to manufacturing methods and tolerances, it is important that the flat rear wall portion be disposed closely to the plane of the skirt 32 so as to abut the chest of a patient slightly beneath the breast while the skirt 32 abuts the chest and abdominal area. Moreover, the rear flat wall portion 44 of the pedestal may have a slight slope, in the order of approximately two degrees, flaring outwardly further at the bottom than at the upper surface 46. The remainder of the wall 44 may have a slight downward slope in the order of approximately two degrees so that the cross sectional configuration of the pedestal 40 is larger at the junction with the surface 38 of the base than at the upper surface 46 so as to provide a localized compression of the breast when the breast is compressed between the upper surface 46 and the paddle 24. It has been found that the spot compression device does not require an opening in the rear skirt 32 described in the aforesaid patent application to obtain satisfactory results since the thickness of the surface 46 is small enough to provide adequate flexibility to permit depression of the back of the pedestal and compression of the posterior aspect of the breast which produces a relative increase in thinning of the breast at the nipple and subareolar. The device as heretofore described may be disposed either on the cover 19 of the platform 18 or directly on the image platform 18 after removal of the cassette holder and moving grid. In either case the upper surface 46 of the pedestal 40 has a clear path to the cover member, thereby providing an air gap between the surface 46 and the cover member.

The compression device 26 preferably is formed from a synthetic plastic material, and it has been found that a transparent copolyester such as a polycarbonate such as that sold under the trademark LEXAN sold by General Electric Company may be used. Alternatively polyethylene Terephthalate Glycol-modified such as that sold under the trademark KODAR by Eastman Chemical Company of Kingsport, Tenn. may be used. These materials not only have a relatively high tensile strength, but have low x-ray radiation absorption characteristics.

A small spot compression and magnification device may have the lower edges of the base coated with a high friction material to preclude the device from moving over the imaging platform or the cover member, but for larger devices, i.e., those having greater magnifications, the device should be firmly attached to the imaging platform or cover. Thus, as illustrated for a large magnification device, the skirts of the base 28 for convenience may be attached to a sub-base 48. The sub-base preferably comprises a front rail 50 secured to a respective end rail 52, 54 by screws or the like 53, the end rails also being secured to a rear rail 56 by screws 55, the front and rear rails being longer than the front and rear skirts 30, 32 by an amount equal to the thickness of the end rails to form lap joints at the connecting interfaces for receiving the respective screws 53, 55 and the spacing between the interior of the end rails 52, 54 is slightly shorter than the length of the platform cover member 19. Additionally, screws or the like (not illustrated) are threaded from the interior of each of the skirts 30, 32, 34, 36 into the respective rail 50, 56, 52, 54 of the sub-base. The end rails 52, 54 and the rear rail 56 have a height which is longer than that of the front rail as best illustrated in FIG. 4 so that when the front rail is disposed on the upper surface of the cover 19, the other rails depend downwardly at the ends and the patient facing surface of the imaging platform cover 19.

Preferably, the bottom of the rear skirt 32 extends downwardly to the level of the lower edge of the rear rail 56, as illustrated in FIG. 4, and a downwardly depending lip member 58 is secured thereto, the lip member 58 extending to a level below the rear and end rails. Thus, the interior of the lip member 58, as illustrated in FIG. 1, may abut the upper portion of the corresponding patient facing surface 59 of the imaging platform cover 19 so as not to slide forwardly due to the action of the patient during the procedure. Moreover, the interior of each of the end rails 52, 54, as illustrated in FIGS. 5 and 6, preferably has an internally projecting ledge 60 spaced slightly above the bottom surface of these rails, the rails being adapted to be received within grooves 62 in those instances where the device 26 is used directly on the imaging platform 18, i.e., where the cassette holder and the moving "Bucky" grid are removed from the mammographic unit 10.

As aforesaid, the device 26 has a substantially truncated pyramid configuration, the height of the base from the surface 38 being approximately 7 inches to the bottom edge of the front rail 50, and approximately 8½ inches to the bottom edges of the remaining rails, the bottom edge of the lip member 58 extending below the bottom edge of the rear rail 56 by approximately ⅜ inch. The wall thickness of the skirts 30, 32, 34, 36 and the surface 38 is approximately ⅛ inch. The opening at the bottom of the device defined between the interior of the rails is approximately 9½ inches by 6 inches while the surface 38 is approximately 6½ inches by 4¾ inches, the front to rear dimensions being smaller than that between the ends. The pedestal 40 preferably is glued or bonded to the surface 38 and has a height of approximately 1 inch, a diameter at the top surface 46 of approximately 3 inches excluding the flat wall surfaces 44, 45 and 47, the former being approximately 2 inches and the other two surfaces being approximately 1½ inches in length so that the front to rear distance across the top surface 46 is in the order of approximately 3 inches, the nominal wall thickness of the surface 46 and the wall 42 of the pedestal being approximately 1/32 of an inch or less. Thus, the total height of the device from the bottom edge of the front rail 50 to the top surface 46 of the pedestal 40 is approximately 8 inches which provides a magnification factor in the order of approximately 1.5. The precise height of the device will depend upon the distance between the x-ray source and the film, and this will vary with the different mammographic machines. Also the thin wall thickness of the pedestal and its mounting provides resiliency and permits sufficient depression of the back of the pedestal and the required compression of the posterior aspect of the breast.

In order to alleviate the need to disassemble the supporting platform, that is the removal of the cassette holder and the moving grid, so that the device 26 may be mounted on the top cover 19 of substantially all mammographic units, the present invention provides adjustable means for tightly clamping and grasping the ends and underside of the cover 19 when the device is in place on the cover. To this end, clamping means in the form of an extendible handle 64, 66 having substantially U-shaped configurations in plan, is carried by the respective end rails 52, 54, the handles being molded from an appropriate synthetic plastic material. Each handle, as illustrated in FIGS. 4 through 6 with respect to the handle 66, has a pair of spaced apart legs 68, 70 which are connected to the respective end rail, e.g. rail 54, by means of a respective rod 72 (only one of which is illustrated). An enlarged head 74 on one end of the respective rod secures the rod to the rail at the interior thereof. The remainder of each rod 72 extends outwardly externally of the rail and is received through a bore 76 in the facing surface of the respective leg 68, 70, the bore 76 opening into a counterbore or hollow 78. Disposed about the rod within the hollow 78 is a coil spring 80 which compresses when the handle is pulled away from the device and thereby stores energy, the spring being constrained between the wall of the hollow 78 adjacent the bore 76 and the head of a screw 82 which is threaded into the adjacent end of the rod 72. A plug 84 closes the end of the hollow remote from the bore 76. Thus, when the handles 64, 66 are pulled away from the device and then released, the handles are urged by the springs into engagement with the respective end rail.

Each leg 68, 70 includes a respective tongue 86, 88 which projects toward the interior of the device 26 and is spaced below the lower edge of the respective end rails 52, 54 as illustrated in FIGS. 5 and 6 with regard to the rail 54 and the lip 88. The spacing between the upper surface or ledge 90 of the tongue 88 and the bottom edge of the rail 54 when the handle abuts the rail is such as to grasp the cassette cover 19 therebetween while the interior facing surface 92 of each of the legs of the handles clamps against the respective end of the cover as the tongues 88 enter into the tunnel 20. Moreover, the handles 64, 66 not only act as clamps but also serve as carrying handles for manipulation of the device.

In use, the device 26 is placed on the cover 19 of the imaging platform 18, the bottom of the front rail resting on the cover and the interior of the rear rail 56 and the lip member 58 abutting and depending downwardly relative to the patient facing surface 59. The end rails are positioned at the edges of the cassette cover and the handles are pulled or extended away from the imaging platform so that the tongues 86, 88 are free of the opening 20. The handles are then released and retract due to the urging of the springs so that the tongues 86, 88 enter into the opening 20 and clamp the cover 19 between the surfaces of the ledges 90 and the bottom edges of the end rails while the surfaces 92 clamp against the respective ends of the cover. The center of the pedestal 40 is then disposed in superposed relationship over the x-ray film. The breast of a patient is then placed on the pedestal with the mass under consideration centered over the center of the pedestal. Pressure is then applied to the upper portion of the breast with the compression paddle 24 compressing the breast between the compression paddle and the device 26. The x-ray cassette is then inserted beneath the device through the space between the bottom edge of the front rail 50 and the cover 19 of the cassette holder.

Accordingly, the present invention provides a spot compression and magnification device which may be positioned readily on the top of the cover of the film cassette holder over the imaging platform. The adjustable handles 64, 66 permit a rapid and simple attachment thereto without requiring removal of the cassette holder containing the moving "Bucky" grid. By being interposed between the breast and the cassette holder devices constructed according to the present invention may be utilized with substantially all the known mammographic units.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A spot compression and magnification device positionable on a surface of a breast supporting platform means of a mammographic apparatus for aiding in the spot compression of the breast of a female patient to provide x-ray images of localized portions of the breast, said device comprising a base having a polygonical cross section configuration including an upper platform and an open bottom defined between upstanding peripheral planar skirts, an aperture formed in said upper platform adjacent the plane of one of said skirts, an upstanding pedestal extending from said platform superposed about said aperture, said pedestal having an upstanding peripheral wall of a substantially circular configuration and a flat top surface adapted for receiving the lower portion of said breast, said pedestal being open at the bottom so that an air gap is formed between said top surface and the surface of said platform means, and said top surface of said pedestal being depressible when said breast is compressed against said flat top.

2. A spot compression and magnification device as recited in claim 1, wherein said pedestal includes a flat surface adjacent said plane of said one skirt for abutting the chest of the patient when said breast is disposed on said flat top.

3. A spot compression and magnification device as recited in claim 1, including adjustable clamping means for adjustably attaching said device to a horizontal wall of said platform means, means including biasing means for connecting said clamping means to said base and for permitting said clamping means to be extended manually from said base and resiliently urged toward said base, said clamping means including tongues disposed below the plane of said open bottom and projecting in a direction toward the interior of said base for engaging a lower surface of said wall of said platform means when said base is positioned on an upper surface of said wall of said platform means.

4. A spot compression and magnification device as recited in claim 3, wherein said clamping means comprises handles having a substantially U-shaped configuration in plan, said handles having legs depending downwardly therefrom, and said tongues being disposed on said legs.

5. A spot compression and magnification device as recited in claim 4, wherein said legs engage and clamp against ends of said wall when said tongues engage the lower surface of said wall.

6. A spot compression and magnification device as recited in claim 4, wherein each of said legs includes a hollow bore, said means for connecting said clamping means to said base comprising a rod having one end fastened to said base and extending into said bore, coil spring means disposed in said bore about said rod, means connected to another end of said rod for trapping said spring means about said rod, said spring means being compressed when said handles are pulled away from said base guided by said rods.

7. A spot compression and magnification device as recited in claim 6, wherein said tongues are disposed adjacent the bottom of said legs.

8. A spot compression and magnification device as recited in claim 5, wherein each of said legs includes a hollow bore, said means for connecting said clamping means to said base comprising a rod having one end fastened to said base and extending into said bore, coil spring means disposed in said bore about said rod, means connected to another end of said rod for trapping said spring means about said rod, said spring means being compressed when said handles are pulled away from said base guided by said rods.

9. A spot compression and magnification device as recited in claim 8, wherein said tongues are disposed adjacent the bottom of said legs.

10. A spot compression and magnification device as recited in claim 2, including adjustable clamping means for adjustably attaching said device to a surface of said platform means, means including biasing means for connecting said clamping means to said base and for permitting said clamping means to be extended manually from said base and resiliently urged toward said base, said clamping means including tongues disposed below the plane of said open bottom and projecting in a direction toward the interior of said base for engaging a lower surface of said wall of said platform means when said base is positioned on an upper surface of said wall of said platform means.

11. A spot compression and magnification device as recited in claim 10, wherein said clamping means comprises handles having a substantially U-shaped configuration in plan, said handles having legs depending downwardly therefrom, and said tongues being disposed on said legs.

12. A spot compression and magnification device as recited in claim 11, wherein said legs engage and clamp against ends of said wall when said tongues engage the lower surface of said wall.

13. A spot compression and magnification device as recited in claim 11, wherein each of said legs includes a hollow bore, said means for connecting said clamping means to said base comprising a rod having one end fastened to said base and extending into said bore, coil spring means disposed in said bore about said rod, means connected to another end of said rod for trapping said spring means about said rod, said spring means being compressed when said handles are pulled away from said base guided by said rods.

14. A spot compression and magnification device as recited in claim 13, wherein said tongues are disposed adjacent the bottom of said legs.

15. A spot compression and magnification device as recited in claim 12, wherein each of said legs includes a hollow bore, said means for connecting said clamping means to said base comprising a rod having one end fastened to said base and extending into said bore, coil spring means disposed in said bore about said rod, means connected to another end of said rod for trapping said spring means about said rod, said spring means being compressed when said handles are pulled away from said base guided by said rods.

16. A spot compression and magnification device as recited in claim 15, wherein said tongues are disposed adjacent the bottom of said legs.

* * * * *